(12) United States Patent
Ulmann

(10) Patent No.: US 9,301,922 B1
(45) Date of Patent: Apr. 5, 2016

(54) STABLE HIGH STRENGTH PHARMACEUTICAL COMPOSITION OF LEVOLEUCOVORIN

(71) Applicant: APROFOL AG, Appenzell Steinegg (CH)

(72) Inventor: Martin Ulmann, Dachsen (CH)

(73) Assignee: APROFOL AG, Appenzell Steinegg (CH)

( * ) Notice: Subject to any disclaimer, the term of this patent is extended or adjusted under 35 U.S.C. 154(b) by 0 days.

(21) Appl. No.: 14/787,984

(22) PCT Filed: Apr. 30, 2014

(86) PCT No.: PCT/EP2014/001152
§ 371 (c)(1),
(2) Date: Oct. 29, 2015

(87) PCT Pub. No.: WO2014/177273
PCT Pub. Date: Nov. 6, 2014

(30) Foreign Application Priority Data

Apr. 30, 2013  (EP) .................... 13002298

(51) Int. Cl.
| | | |
|---|---|---|
| *A61K 31/519* | (2006.01) | |
| *A61K 9/08* | (2006.01) | |
| *A61K 47/18* | (2006.01) | |
| *A61K 47/20* | (2006.01) | |
| *A61K 47/12* | (2006.01) | |
| *A61K 47/24* | (2006.01) | |

(52) U.S. Cl.
CPC ................. *A61K 9/08* (2013.01); *A61K 31/519* (2013.01); *A61K 47/12* (2013.01); *A61K 47/18* (2013.01); *A61K 47/20* (2013.01); *A61K 47/24* (2013.01)

(58) Field of Classification Search
USPC ....................................................... 514/249
See application file for complete search history.

(56) References Cited

U.S. PATENT DOCUMENTS

| 4,931,441 A | 6/1990 | Lawrence |
|---|---|---|
| 2007/0099866 A1 | 5/2007 | Moser |

FOREIGN PATENT DOCUMENTS

| EP | 0416232 | 3/1991 |
|---|---|---|
| EP | 1640008 | 3/2006 |
| WO | 0191734 | 12/2001 |
| WO | 2004112761 | 12/2004 |
| WO | 2010043050 | 4/2010 |

OTHER PUBLICATIONS

"Guidance for Industry," Q1A (R2) "Stability Testing of New Drug Substances and Products," Nov. 2003, pp. 1-22, U.S. Department of Health and Human Services, Food and Drug Administration.
"Particulate Matter in Injections," U. S. Pharmacopeial Convention, Revised Bulletin, Official Jul. 1, 2012, pp. 1-3.
European Search Report for European Application No. 13002298.1-1460 mailed Jul. 1, 2013.
European Search Report for European Application No. 13002299.9-1460 mailed Jul. 1, 2013.
International Search Report for International Application No. PCT/EP2014/001152 mailed Jun. 5, 2014.
International Search Report for International Application No. PCT/EP2014/001153 mailed Jun. 6, 2014.
Written Opinion of the International Searching Authority for International Application No. PCT/EP2014/001152 mailed Jun. 5, 2014.
Written Opinion of the International Searching Authority for International Application No. PCT/EP2014/001153 mailed Jun. 6, 2014.

*Primary Examiner* — Kristin Vajda
(74) *Attorney, Agent, or Firm* — RatnerPrestia

(57) ABSTRACT

The administration of levoleucovorin is useful as an antidote to drugs which act as folic acid antagonists and in combination chemotherapy with 5-FU. The most often used calcium salt of levoleucovorin has a limited solubility in water and forms almost insoluble degradation products. Therefore aqueous solutions are unstable and precipitates are resulting. Precipitates in injectable products present an unacceptable safety risk to patients. Stable high strength pharmaceutical aqueous compositions containing calcium salts, magnesium or zinc salts of levoleucovorin and one or more of the compounds sodium gluconate, potassium gluconate, glycerophosphate disodium salt or glycerophosphate dipotassium salt are disclosed.

20 Claims, No Drawings

STABLE HIGH STRENGTH PHARMACEUTICAL COMPOSITION OF LEVOLEUCOVORIN

CROSS-REFERENCE TO RELATED APPLICATIONS

This application is a national phase of International application PCT/EP2014/001152, filed Apr. 30, 2014, which claims priority from European application 13002298.1, filed Apr. 30, 2013. The disclosures of each of these applications are incorporated herein by reference

FIELD OF THE INVENTION

This invention relates to stable high strength pharmaceutical aqueous compositions containing levoleucovorin.

BACKGROUND OF THE RELATED ART

Levoleucovorin salts, in particular levoleucovorin calcium, are drug substances containing 5-formyl-(6S)-tetrahydrofolate or levofolinic acid.

The administration of levoleucovorin is useful as an antidote to drugs which act as folic acid antagonists and as dihydrofolate reductase inhibitors. Levoleucovorin is used as well in combination chemotherapy with 5-FU in the treatment of patients with e.g. metastatic colorectal cancer. In cancer chemotherapy typically levoleucovorin is administered intravenously in 5 to 10 mg levofolinic acid per ml aqueous solution. Stability of these aqueous solutions is limited due to oxidative degradation which yields almost insoluble degradation compounds and thus precipitates. More importantly, levoleucovorin and specifically its calcium salt have a low solubility in water and tend to form supersaturated solutions which are likely to form precipitates during storage. Therefore aqueous solutions are unstable and may form precipitates during handling and storage. The appearance of such precipitates in drug products intended for intravenous administration constitutes "Particulate Matter", a critical quality defect and a significant risk for patients resulting in a recall of the affected drug products. Oxidative degradation of levoleucovorin is minimized if the initial solution is freeze-dried under nitrogen blanket and packaged in vials as a lyophilized powder. The product is then reconstituted before use with a diluent (e.g. water for injection, 0.9% sodium chloride or 5% dextrose solution). However, limited solubility restricts the preparation of high strength compositions, for the "ready-to-use solution" as well as the reconstituted "lyophilized powder" form. In view of these stability issues, many of the levoleucovorin containing drug products are used as reconstituted solutions made from "lyophilized powder". There are "ready-to-use" solutions on the market which require a strict cold chain control during the entire distribution cycle (e.g. transport, warehouse, storage). The shelf life of the drug products is directly related to the degree of oxidative degradation of the drug substance, and to precipitation of less soluble degradation products. The limited aqueous solubility and possibility of precipitation dictates the limited concentration of the drug substance in the formulation and reconstituted solution. The principle reasons for the formation of particulate matter are: the crystallization of the drug substance in the supersaturated solution, and the degradation of the drug substance forming less soluble compounds which precipitate, both resulting in particulate matter.

US 2007/0099866 proposes a stable pharmaceutical composition of 5,10-methylene-tetrahydrofolate with citrate formulated in a pH range between 7.5 and 10.5. The formulations are particularly suitable for producing lyophilization solutions and lyophilizates or dry powders and dry mixtures. The lyophilizates must be reconstituted by adding suitable diluents to prepare for intravenous administration. An aqueous preparation for injection is disclosed in EP 1 640 008 consisting of 5-formyl-(6S)-tetrahydrofolic acid with a basification material or a buffer agent and an antioxidant, for example ascorbic acid. U.S. Pat. No. 4,931,441 discloses an aqueous leucovorin calcium (5-formyl-(6R,S)-tetrahydrofolic acid, calcium salt) solution in the amount of 6.35 mg per ml of solution (5 mg per ml as the free acid). The low concentration of the solution reduces the benefit of the medication during administration. A stable, injectable aqueous composition comprising a salt of folic acid or leucovorin is described in EP 0 416 232. The compound benzyl alcohol is required to preserve and stabilize the composition.

For therapeutic use such pharmaceutical compositions comprise a therapeutically effective amount sufficient for the treatment of patients. As indicated herein, it is important in the preparation of aqueous injectable solutions, that these drug products are made available to the patient in a stable high strength form without the risk of particulate matter formation. According to the instant invention, compositions as defined in the independent claim 1 have been developed to meet such requirements. Preferred embodiments are subject to the dependent claims.

The term "drug product" as used herein means a finished dosage form, for example, tablet, capsule, or solution, that contains a drug substance, generally, but not necessarily, in association with one or more other ingredients.

The term "drug substance" or "active pharmaceutical ingredient (API)" as used herein means an active ingredient that is intended to furnish pharmacological activity or other direct effect in the diagnosis, cure, mitigation, treatment, or prevention of disease or to affect the structure or any function of the human body.

The term "stable" as used herein means that the solution comprising the reduced folates does not form any precipitates and/or crystals over a prolonged period of time, that is, over a period of time of e.g., three years. Stability thus refers to the stability of the solution to remain free of particulate matter over the entire period of their shelf live. Further details on the stability of drug products are found in "Guidance for Industry", Q1A (R2) "Stability Testing of New Drug Substances and Products" (November 2003), section 2.2, in particular 2.2.5 "Specification" and 2.2.7 "General Case". For the determination of particulate matter a Microscopic Particle Count Test as described in Particulate Matter in Injections, United States Pharmacopeial Convention, Revision Bulletin, Official Jul. 1, 2012 may be used.

The term "high strength" as used herein refers to solutions comprising at least 7 mg/ml of levoleucovorin (calculated as free acid).

SUMMARY OF THE INVENTION

Pharmaceutical aqueous compositions according to the instant invention comprise the calcium salt, magnesium salt or zinc salt of levoleucovorin, and one or more of the compounds sodium gluconate, potassium gluconate, sodium lactate, potassium lactate, glycerophosphate disodium salt or glycerophosphate dipotassium salt. The compositions optionally comprise a pharmaceutically acceptable buffer compound and/or a pharmaceutically acceptable antioxidant compound.

DETAILED DESCRIPTION OF CERTAIN EMBODIMENTS OF THE INVENTION

The most preferred compounds are sodium gluconate, potassium gluconate, glycerophosphate disodium salt and glycerophosphate dipotassium salt. Least preferred compounds are the sodium and the potassium salt of lactate.

In a preferred embodiment the composition according to the present invention comprises a buffer compound selected from the group consisting of trometamol (tris(hydroxymethyl)aminomethane) and HEPES (2-[4-(2-hydroxyethyl) piperazine]ethanesulfonic acid). Trometamol is the preferred buffer compound. Buffering the pharmaceutical aqueous compositions according to the present invention in the preferred range of pH 7.4 to pH 8.1 significantly stabilizes the aqueous composition and greatly reduces the formation of particulate matter.

In another preferred embodiment the composition comprises the buffer compound in a concentration range of 5 to 50 mM, preferably in a concentration range of 10 to 25 mM.

In a further preferred embodiment the composition comprises an antioxidant compound selected from the group of thioglycerol, dithiothreitol (DTT) and cysteine. The most preferred antioxidant compound is thioglycerol while cysteine is the least preferred antioxidant compound. The preferred amount of the antioxidant compound is in the range of 0.1% to 1.0% (w/v), more preferably in the range of 0.3% to 0.8% (w/v), most preferably in the range of 0.4% to 0.6% (w/v).

The amount of thioglycerol in the pharmaceutical aqueous composition is in the range of 0.1% to 1.0% (w/v). Preferably the amount of thioglycerol is in the range of 0.3% to 0.8% (w/v), more preferably in the range of 0.4% to 0.6% (w/v).

The compositions according to the instant invention are aqueous compositions comprising levoleucovorin as disclosed above. The aqueous compositions remain stable for prolonged periods of time under refrigerated or room temperature storage conditions. Even after prolonged periods, no precipitation or crystallization is observed. Typical storage periods, at room temperatures of 15° to 25° C. or refrigerated at temperatures of 2° to 8° C. may extend for tests by way of example over 7, 15, 30, 60 or 120 days and in practice may last up to the end of the shelf life, for instance 12, 24 or 36 months. The aqueous solution can be filled and stored as a freeze-dried (lyophilized) powder to be reconstituted to a set concentration for administration, or can be produced in a "ready to use" concentration in containers, like e.g. vials or ampoules. Drug products in the final form can be administered either intramuscularly or intravenously. The composition may or may not contain additional excipients. Preferably the compositions are free of compounds such as benzyl alcohol. Excipients such as mannitol for acceptable cake formation during the freeze-drying process, or sodium chloride and dextrose to adjust for osmolarity may be added to the compositions. The pH of the solutions is typically in the range of 6.5 to 8.5, preferably in the range of 7.4 to 8.1 and can be adjusted during drug product manufacturing with e.g. small amount of hydrochloric acid or sodium hydroxide. The solution may contain a buffer compound and/or an antioxidant to prevent oxidative degradation of levoleucovorin.

Pharmaceutical aqueous compositions according to the present invention remain surprisingly stable for a prolonged period of time in terms of particulate matter from the drug substance. The preferred combination of salts of gluconate, lactate or glycerophosphate with a buffer compound and/or an antioxidant compound further improves the solubility of levoleucovorin and also stabilizes levoleucovorin in aqueous compositions thus almost eliminating the risk of particulate matter caused by degradation products.

In the composition at least one additional compound, like the calcium salt, magnesium salt or zinc salt of leucovorin, (6R,S)-tetrahydrofolic acid, (6S)-tetrahydrofolic acid, 5,10-methylene-(6R,S)-tetrahydrofolate, 5,10-methylene-(6R)-tetrahydrofolate, 5-methyl-(6R,S)-tetrahydrofolate or 5-methyl-(6S)-tetrahydrofolate or a mixture of 2, 3 or more of said compounds can be used.

Preferred compositions comprise the calcium salt of levoleucovorin.

Preferred compositions according to the instant invention comprise one or more of the compounds sodium gluconate, potassium gluconate, sodium lactate, potassium lactate, glycerophosphate dipotassium salt or glycerophosphate disodium salt. Most preferred compositions comprise one or more of the compounds sodium gluconate, potassium gluconate, glycerophosphate dipotassium salt or glycerophosphate disodium salt.

Regarding the amounts of the compounds in the compositions the following ratios are preferred. The compositions preferably contain for one mole of the calcium salts, magnesium salts or zinc salts of levoleucovorin, 0.8 to 6.0 moles, advantageously 1.0 to 4.0 moles, of sodium gluconate, potassium gluconate, sodium lactate or potassium lactate. In a practical embodiment the compositions preferably contain for one mole of the calcium salts, magnesium salts or zinc salts of levoleucovorin, 1.5 to 3.0 moles of sodium gluconate or potassium gluconate. Such a composition may contain for one mole levoleucovorin a minimum of 0.8, preferred of 1.0 moles, advantageous 1.5 moles, and a maximum of 6.0 moles, preferably of 4.0 moles, advantageous 3.0 moles, of sodium gluconate, potassium gluconate, sodium lactate or potassium lactate.

Other compositions preferably contain for one mole of the calcium salts, magnesium salts or zinc salts of levoleucovorin, 0.4 to 4.0 moles, preferably 0.5 to 3.0 moles, advantageously 0.7 to 2.0, of glycerophosphate disodium salt or glycerophosphate dipotassium salt. Such a composition may contain for one mole of levoleucovorin a minimum of 0.4, preferred of 0.5 moles, advantageously 0.7 moles and a maximum of 4.0 moles, preferably of 3.0 moles, advantageously of 2.0 moles of glycerophosphate disodium salt or glycerophosphate dipotassium salt.

Preferred aqueous compositions according to the instant invention comprising 7 to 300 mg, preferably 10 to 100 mg, advantageously 20 to 50 mg, calcium salts, magnesium salts or zinc salts of levoleucovorin, in 1 ml water (calculated as the free acid). In other words, such compositions may contain a minimum of 7 mg and preferably 20 mg, and a maximum of 300, preferably of 100 mg advantageously of 50 mg, calcium salts, magnesium salts or zinc salts of levoleucovorin, in 1 ml water.

Advantageous aqueous compositions comprise 7 to 100 mg, preferably 20 to 50 mg, calcium salts, magnesium salts or zinc salts of levoleucovorin, in 1 ml water (calculated as the free acid) and the 0.8 to 6.0 molar, preferably 1.0 to 4.0 molar, amount of sodium gluconate, potassium gluconate, sodium lactate or potassium lactate.

Other advantageous aqueous compositions comprise 7 to 100 mg, preferably 20 to 50 mg, calcium salts, magnesium salts or zinc salts of levoleucovorin, in 1 ml water (calculated as the free acid) and the 0.4 to 4.0 molar, preferably 0.5 to 3.0 molar, amount of glycerophosphate disodium salt or glycerophosphate dipotassium salt.

Preferred are stable high strength pharmaceutical aqueous compositions comprising 7 to 100 mg, advantageously 20 to 50 mg per ml of the calcium salt of levoleucovorin (Levoleucovorin Calcium, calculated as the free acid) and the 1.5 to 3.0 molar amount of sodium gluconate.

Another preferred embodiment are stable high strength pharmaceutical aqueous compositions whereby the composition comprises 50 to 300 mg, preferably 100 to 200 mg, calcium salts, magnesium salts or zinc salts of levoleucovorin, in 1 ml water (calculated as the free acid) and a 1.5 to 3.0 molar amount of sodium gluconate, potassium gluconate, sodium lactate or potassium lactate. Sodium gluconate and potassium gluconate are preferred. Other stable high strength pharmaceutical aqueous compositions may comprise 50 to 300 mg, preferably 100 to 200 mg, calcium salts, magnesium salts or zinc salts of levoleucovorin in 1 ml water (calculated as the free acid) and a 0.4 to 4.0 molar, preferably 0.5 to 3.0 molar, amount of glycerophosphate disodium salt or glycerophosphate dipotassium salt. All such compositions show a very high concentration of levoleucovorin. In practice the compositions have to be reconstituted with a diluent, like an aqueous diluent, before use or administration. Compositions with a very high concentration may be used instead of lyophilized powders.

The weights of levoleucovorin given above are calculated as the free acid.

The inventive compositions may or may not contain additional excipients and antioxidants, and might be adjusted to a pH of 6.5 to 8.5, preferably to a pH of 7.4 to 8.1.

The pharmaceutical aqueous compositions according to the present invention may be used to manufacture a lyophilized powder.

Lyophilized powder is a dosage form intended for injection prepared by lyophilization ("freeze drying"), a process which involves the removal of water from products in the frozen state at extremely low pressures; this is intended for subsequent reconstitution with liquid to create a solution that conforms in all respects to the requirements for injections. While lyophilized powders made of pharmaceutical aqueous compositions comprising levoleucovorin according to the present invention may be stored at room temperature, the "ready to use" pharmaceutical aqueous solutions are preferably stored at a refrigerator at 2° C. to 8° C.

The instant invention is illustrated further by the examples.

Examples 1 to 19

The following method is used for the preparation of the examples 1 to 19 listed in Table 1. The amount of (x) mg of the calcium salt of levoleucovorin is dissolved at temperatures of about 20° C. in 10 ml of solvent containing (y) mg of the excipient. The amount of the excipient is first dissolved in 10 ml purified water. Depending on the conditions, the temperature is increased to about 40° C. to obtain a clear solution. The clear solution was filtered with a 0.45 μm filter and divided in two parts. One part is stored in the refrigerator at 2° to 8° C., the other one kept at room temperature at 15° to 25° C. The storage conditions and storage times applied are disclosed in columns "storage, room temperature" and "storage refrigerator". At the end of the test period the samples are checked and rated. The rating "clear" is used, if composition remains clear and no precipitation is visible in the fluid of the test sample. "Cryst." is used in case a precipitate in the fluid or at the bottom of the test vial is visible. In an additional test the samples are stored for 7 days and are seeded with a few crystals of the calcium salt of levoleucovorin. The crystallization characteristics are observed 24 hours after seeding. In column "storage, refrigerator, seeding" the results are recorded. A rating "seed" means, the seeding crystals remain, but do not initiate a precipitation. A rating "clear" means the seeding crystals dissolve and the composition is clear again.

In Table 1, 2 and 3 "Na-Glc" indicates sodium gluconate, "Na-Lac" indicates sodium lactate, "K-Glc" indicates potassium gluconate and "Gly" indicates glycerophosphate disodium salt. "Thio" indicates thioglycerol and "DTT" indicates dithiothreitol.

Table 2 shows the examples 1 to 19 whereby the storage period at room temperature has been extended to two months. The results demonstrate that none of the examples shows any precipitation or particulate matter.

For a limited number of examples (no. 11 to 18) the storage at 2° C.-8° C. (referred to as storage refrigerator) has been done for an extended period of time. After 10 months these examples still did not show any precipitation or crystallization.

Example 20

4.0 g of levoleucovorin calcium (6.7 mmol) are suspended in 100 ml water. The slurry is heated up to about 40° C. to obtain a clear solution. 1.0 g of zinc acetate dihydrate (4.6 mmol) in 10 ml water is slowly added. A precipitate is formed immediately. After one day the precipitate is separated from the mother liquor. Yield: 2.5 g levoleucovorin zinc (4.0 mmol), almost insoluble in water.

0.4 g of the above levoleucovorin zinc is added to a solution containing 1.0 g potassium gluconate in 30 ml water. After 15 minutes a clear solution is obtained forming no precipitate over 10 days at room temperature.

Example 21

3.0 g of levoleucovorin calcium are dissolved at a temperature of about 20° C. in a solvent containing 2.88 g of sodium gluconate. The amount of the excipient is first dissolved in 10 ml purified water. A clear solution is obtained at about 25° C. The clear solution is filtered with a 0.45 μm filter and divided in two parts. One part is stored in the refrigerator at 2° C. to 8° C., the other one kept at room temperature at 15° C. to 25° C. No precipitation or crystallization occurs neither at room temperature nor in the refrigerator.

Examples 22 to 27

The following method is used for the preparation of the examples 22 to 27 listed in Table 3.

(x) mg/ml of the calcium salt of levoleucovorin are dissolved at temperatures of about 20° C. in 40 ml of solvent containing (y) molar amount of sodium gluconate. The excipient is first dissolved in 40 ml purified water. Optionally the buffer compound and/or the antioxidant in the given concentration are added.

Depending on the conditions, the temperature is increased to about 40° C. to obtain a clear solution. The pH is adjusted to a range in between 7.4 to 8.1 with hydrochloric acid or sodium hydroxide. The clear solution is filtered with a 0.45

µm filter and divided in different parts. One part was stored in the refrigerator at 4° C., another one kept at room temperature at 25° C. respectively at 40° C. (stress test). The solutions at 40° C. (stress test) are analysed with HPLC after 60 days.

Table 3 shows the results for examples 22 to 27. The compositions comprise the compounds as indicated in table 3. The samples were stored for 60 days at 40° C. (stress test). After the storage period the samples are analysed to measure the amount of levoleucovorin. Samples comprising levoleucovorin alone were used as comparison. The measurement was performed according to the method described in US Pharmacopeia 35, monograph leucovorin calcium tablets, pages 3651-3652. In brief, the samples were analysed by HPLC on RP-C18 column (4.6 mm×150 mm). The mobile phase was 0.005M tetrabutylammonium-phosphate in water and methanol (80:20) at a flow rate of 2 ml/min. Detection was done by UV measurement at a wavelength of 254 nm. The amount of levoleucovorin is indicated as percentage of the initial amount. The quantitative assay was calculated according to USP 35 (% w/v, external standard).

TABLE 1

| No. | Amount Levoleucovorin ("LL") (x) mg per 10 ml | Amount Levoleucovorin ("LL") in mg per ml, based on the free acid | Excipient ("E") Name | (y) mg per 10 ml | Ratio mol LL/ mol E | Storage room temp. 15 days | Storage refrigerator 7 days | Storage refrigerator seeding |
|---|---|---|---|---|---|---|---|---|
| 1  | 133  | 10  | Na-Glc | 48   | 1 to 1 | clear | clear | seed  |
| 2  | 333  | 25  | Na-Glc | 120  | 1 to 1 | clear | clear | seed  |
| 3  | 333  | 25  | Na-Lac | 103  | 1 to 1 | clear | clear | seed  |
| 4  | 666  | 50  | Na-Glc | 240  | 1 to 1 | clear | clear | seed  |
| 5  | 333  | 25  | Na-Glc | 240  | 1 to 2 | clear | clear | clear |
| 6  | 666  | 50  | Na-Glc | 480  | 1 to 2 | clear | clear | clear |
| 7  | 666  | 50  | Na-Glc | 240  | 1 to 1 | clear | clear | seed  |
| 8  | 666  | 50  | Na-Glc | 480  | 1 to 2 | clear | clear | seed  |
| 9  | 1333 | 100 | Na-Glc | 1440 | 1 to 3 | clear | clear | clear |
| 10 | 1333 | 100 | Na-Glc | 960  | 1 to 2 | clear | clear | clear |
| 11 | 333  | 25  | Na-Glc | 240  | 1 to 2 | clear | clear | seed  |
| 12 | 333  | 25  | Na-Glc | 480  | 1 to 4 | clear | clear | clear |
| 13 | 666  | 50  | Na-Glc | 960  | 1 to 4 | clear | clear | clear |
| 14 | 666  | 50  | Na-Lac | 417  | 1 to 2 | clear | clear | seed  |
| 15 | 666  | 50  | K-Glc  | 520  | 1 to 2 | clear | clear | seed  |
| 16 | 333  | 25  | Na-Lac | 410  | 1 to 4 | clear | clear | seed  |
| 17 | 333  | 25  | Gly    | 500  | 1 to 4 | clear | clear | seed  |
| 18 | 333  | 25  | K-Glc  | 520  | 1 to 4 | clear | clear | seed  |
| 19 | 1333 | 100 | Na-Glc | 1920 | 1 to 4 | clear | clear | clear |

TABLE 2

| No. | Amount Levoleucovorin ("LL") (x) mg per 10 ml | Amount Levoleucovorin ("LL") in mg per ml, based on the free acid | Excipient ("E") Name | (y) mg per 10 ml | Ratio mol LL/ mol E | Storage room temp. 15 days | Storage room temp. 2 months |
|---|---|---|---|---|---|---|---|
| 1  | 133  | 10  | Na-Glc | 48   | 1 to 1 | clear | clear |
| 2  | 333  | 25  | Na-Glc | 120  | 1 to 1 | clear | clear |
| 3  | 333  | 25  | Na-Lac | 103  | 1 to 1 | clear | clear |
| 4  | 666  | 50  | Na-Glc | 240  | 1 to 1 | clear | clear |
| 5  | 333  | 25  | Na-Glc | 240  | 1 to 2 | clear | clear |
| 6  | 666  | 50  | Na-Glc | 480  | 1 to 2 | clear | clear |
| 7  | 666  | 50  | Na-Glc | 240  | 1 to 1 | clear | clear |
| 8  | 666  | 50  | Na-Glc | 480  | 1 to 2 | clear | clear |
| 9  | 1333 | 100 | Na-Glc | 1440 | 1 to 3 | clear | clear |
| 10 | 1333 | 100 | Na-Glc | 960  | 1 to 2 | clear | clear |
| 11 | 333  | 25  | Na-Glc | 240  | 1 to 2 | clear | clear |
| 12 | 333  | 25  | Na-Glc | 480  | 1 to 4 | clear | clear |
| 13 | 666  | 50  | Na-Glc | 960  | 1 to 4 | clear | clear |
| 14 | 666  | 50  | Na-Lac | 417  | 1 to 2 | clear | clear |
| 15 | 666  | 50  | K-Glc  | 520  | 1 to 2 | clear | clear |
| 16 | 333  | 25  | Na-Lac | 410  | 1 to 4 | clear | clear |
| 17 | 333  | 25  | Gly    | 500  | 1 to 4 | clear | clear |
| 18 | 333  | 25  | K-Glc  | 520  | 1 to 4 | clear | clear |
| 19 | 1333 | 100 | Na-Glc | 1920 | 1 to 4 | clear | clear |

TABLE 3

Stability of Levoleucovorin Solutions after 60 days at 40° C.

| No. | Concentration mg/mL as levofolinic acid | Excipients Na-Glc molar ratio | Buffer Trometamol mg/mL | Antioxidant | Assay % |
|---|---|---|---|---|---|
| 22 | 10 | without | 0 | 0 | 77.5 |
| 23 | 20 | 1:1.6 | 5 | 0.5% Thio | 83.3 |
| 24 | 20 | 1:1.6 | 3 | 0.5% Thio | 81.5 |
| 25 | 20 | 1:1.6 | 3 | 0.5% DTT | 89.9 |
| 26 | 20 | 1:1.6 | 3 | 0.5% Cystein | 87.0 |
| 27 | 10 | 1:2 | 3 | 0.5% Thio | 88.7 |

The invention claimed is:

1. A pharmaceutical aqueous composition containing levoleucovorin, wherein the composition comprises the calcium salt, magnesium salt or zinc salt of levoleucovorin, optionally a pharmaceutically acceptable buffer compound, optionally a pharmaceutically acceptable antioxidant compound and one or more of the compounds sodium gluconate, potassium gluconate, glycerophosphate disodium salt or glycerophosphate dipotassium salt.

2. The pharmaceutical aqueous composition according to claim 1, wherein the composition comprises a pharmaceutically acceptable buffer compound and the buffer compound is selected from the group consisting of trometamol and HEPES.

3. The pharmaceutical aqueous composition according to claim 2, wherein the composition comprises the buffer compound in a concentration range of 5 to 50 mM.

4. The pharmaceutical aqueous composition according to claim 1, wherein the composition comprises a pharmaceutically acceptable antioxidant compound and the antioxidant compound is selected from the group consisting of thioglycerol, dithiothreitol and cysteine in a concentration range of 0.1% to 1.0% (w/v).

5. The pharmaceutical aqueous composition according to claim 1, wherein the composition contains for one mole of the calcium salt, magnesium salt or zinc salt of levoleucovorin 0.8 to 6.0 moles of sodium gluconate or potassium gluconate.

6. The pharmaceutical aqueous composition according to claim 1, wherein the composition contains for one mole of the calcium salt, magnesium salt or zinc salt of levoleucovorin 0.4 to 4.0 moles of glycerophosphate disodium salt or glycerophosphate dipotassium salt.

7. The pharmaceutical aqueous composition according to claim 1, wherein the composition comprises 7 to 300 mg calcium salt, magnesium salt or zinc salt of levoleucovorin in 1 ml water (calculated as the free acid).

8. The pharmaceutical aqueous composition according to claim 1, wherein the composition comprises 7 to 100 mg calcium salt, magnesium salt or zinc salt of levoleucovorin in 1 ml water (calculated as the free acid) and a 0.8 to 6.0 molar amount of sodium gluconate or potassium gluconate.

9. The pharmaceutical aqueous composition according to claim 1, wherein the composition comprises 7 to 100 mg calcium salt, magnesium salt or zinc salt of levoleucovorin in 1 ml water (calculated as the free acid) and a 0.4 to 4.0 molar amount of glycerophosphate disodium salt or glycerophosphate dipotassium salt.

10. The pharmaceutical aqueous composition according to claim 1, wherein the composition comprises 7 to 100 mg of the calcium salt of levoleucovorin (Levoleucovorin Calcium, calculated as the free levofolinic acid) and a 1.5 to 3.0 molar amount of sodium gluconate or potassium gluconate.

11. The pharmaceutical aqueous composition according to claim 1, wherein the composition comprises 50 to 300 mg calcium salt, magnesium salt or zinc salt of levoleucovorin in 1 ml water (calculated as the free acid) and a 1.5 to 3.0 molar amount of sodium gluconate or potassium gluconate.

12. The pharmaceutical aqueous composition according to claim 1, wherein the composition comprises 50 to 300 mg calcium salt, magnesium salt or zinc salt of levoleucovorin in 1 ml water (calculated as the free acid) and a 0.4 to 4.0 molar amount of glycerophosphate disodium salt or glycerophosphate dipotassium salt.

13. A method of manufacturing a lyophilized powder, comprising lyophilizing the pharmaceutical aqueous composition of claim 1.

14. The pharmaceutical aqueous composition according to claim 2, wherein the composition comprises the buffer compound in a concentration range of 10 to 25 mM.

15. The pharmaceutical aqueous composition according to claim 1, wherein the composition comprises a pharmaceutically acceptable antioxidant compound and the antioxidant compound is selected from the group consisting of thioglycerol, dithiothreitol and cysteine in a concentration range of 0.3% to 0.8% (w/v).

16. The pharmaceutical aqueous composition according to claim 1, wherein the composition contains for one mole of the calcium salt, magnesium salt or zinc salt of levoleucovorin 1.0 to 4.0 moles of sodium gluconate or potassium gluconate.

17. The pharmaceutical aqueous composition according to claim 1, wherein the composition contains for one mole of the calcium salt, magnesium salt or zinc salt of levoleucovorin 0.5 to 3 moles of glycerophosphate disodium salt or glycerophosphate dipotassium salt.

18. The pharmaceutical aqueous composition according to claim 1, wherein the composition comprises 20 to 200 mg calcium salt, magnesium salt or zinc salt of levoleucovorin in 1 ml water (calculated as the free acid).

19. The pharmaceutical aqueous composition according to claim 1, wherein the composition comprises 20 to 50 mg calcium salt, magnesium salt or zinc salt of levoleucovorin in 1 ml water (calculated as the free acid) and a 1.0 to 4.0 molar amount of sodium gluconate or potassium gluconate.

20. The pharmaceutical aqueous composition according to claim 1, wherein the composition comprises 20 to 50 mg calcium salt, magnesium salt or zinc salt of levoleucovorin in 1 ml water (calculated as the free acid) and a 0.5 to 3.0 molar amount of glycerophosphate disodium salt or glycerophosphate dipotassium salt.

* * * * *